United States Patent [19]

Smith et al.

[11] 4,045,558

[45] Aug. 30, 1977

[54] PILOCARPINE SALTS

[75] Inventors: Robert L. Smith; Ta-Jyh Lee, both of Lansdale, Pa.

[73] Assignee: Merck & Co., Inc., Rayway, N.J.

[21] Appl. No.: 620,623

[22] Filed: Oct. 8, 1975

[51] Int. Cl.$^2$ .................. A61K 31/62; A61K 31/672; A61K 31/415; C07D 405/06
[52] U.S. Cl. .................................. 424/232; 548/336; 424/200; 424/273 R
[58] Field of Search .................... 260/309; 424/14, 16, 424/19-22, 28, 35, 200, 273, 232, 362

[56] References Cited

U.S. PATENT DOCUMENTS

| | | | |
|---|---|---|---|
| 3,450,814 | 6/1969 | Bechtold et al. | 424/279 |
| 3,845,201 | 10/1974 | Haddad et al. | 424/22 |
| 3,875,300 | 4/1975 | Homm et al. | 128/260 |

FOREIGN PATENT DOCUMENTS

| | | | |
|---|---|---|---|
| 1,090,492 | 11/1967 | United Kingdom | 260/309 |

OTHER PUBLICATIONS

Loucas et al. J. Pharm. Science 1972, vol. 61, pp. 985-986.
The Merck Index 8th Ed. p. 833 Rahway, N. J., Merck & Co., 1968.
Massatsch Chem. Abst. 1948, vol. 42, column 7935.
Yavors'kii Chem. Abst. 1964, vol. 61, column 9361.
Purvis Chem. Abst. 1928, vol. 22, p. 786.

*Primary Examiner*—Natalie Trousof
*Attorney, Agent, or Firm*—Mario A. Monaco; Harry E. Westlake, Jr.

[57] ABSTRACT

Pilocarpinium 2-naphthalenesulfonate, pilocarpinium 2,5-dihydroxybenzoate, pilocarpinium dihydrogenphosphate, pilocarpinium 2-chloro-4,6-disulfamoylphenoxide, and pilocarpinium 3,5-di-tert-butylsalicylate, novel compounds effective in the treatment of glaucoma.

5 Claims, No Drawings

PILOCARPINE SALTS

BACKGROUND OF THE INVENTION

The present invention is directed to novel antiglaucoma agents which are effective in lowering intraocular pressure in the human as well as animal eye, to compositions containing these novel compounds and to their administration as well as to methods for preparing these novel compounds.

One of the present therapeutic methods for the treatment of glaucoma usually involves the use of miotics such as pilocarpine or the corresponding hydrochloride or nitrate salt. These drugs when employed in a solid insert such as hydroxypropyl cellulose are difficult to formulate. We have found certain novel pilocarpine salts which can be more readily formulated into solid inserts and have the added advantage of having a longer duration of action.

DETAILS OF THE INVENTION

The present invention relates to novel pilocarpine acid addition salts effective in the treatment of glaucoma. More specifically, the invention is directed to pilocarpinium 2-naphthalenesulfonate, pilocarpinium 2,5-dihydroxybenzoate, pilocarpinium dihydrogenphosphate, pilocarpinium 2-chloro-4,6-disulfamoylphenoxide, and pilocarpinium 3,5-di-tert-butylsalicylate as novel compounds useful in the treatment of glaucoma, to compositions containing these novel compounds, to a method of treating glaucoma and to a process for preparing these novel compounds.

The compounds of this invention are preferably administered in the form of ophthalmic pharmaceutical preparations adapted for topical administration to the eye, such as solutions, ointments or ocular inserts. Formulations of these novel compounds may contain unit dosages of from 1 to 15% and especially 5 to 8% of the solution or ointment. Higher dosages as, for example, about 10% or lower dosages can be employed provided the dose is effective in lowering intraocular pressure. When the compounds are administered in the form of solid inserts, they comprise between 5 to 15% by weight of the solid insert.

The pharmaceutical preparation which contains the compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene gylcols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,5000, 4,000 and 10,000, bacterial components such as quaternary ammonium compounds, phenylmercuric salts known to have cold sterilizing properties and which are non-injurious in use, thimerosal, propyl paraben, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles, and the like. The compounds may also be administered in the form of a water soluble solid polymer insert. The polymer used to form the inserts may be any water soluble non-toxic polymer. For example, one may employ water soluble polymers of cellulose derivatives such as methylcellulose, sodium carboxymethyl cellulose (hydroxyloweralkyl cellulose), hydroxyethyl cellulose, hydroxypropyl cellulose, hydroxypropyl cellulose, hydroxypropylmethyl cellulose; acrylates such as polyacrylic acid salts, ethylacrylates, polyacrylamides; natural products such as gelatin, alginates, pectins, tragacanth, karaya, chondrus, agar, acacia; the starch derivatives such as starch acetate, hydroxyethyl starch ethers, hydroxypropyl starch, as well as othr synthetic derivatives such as polyvinyl alcohol, polyvinyl pyrrolidone, polyvinyl methyl ether, polyethylene oxide, neutralized carbopol and xanthan gum, and mixtures of said polymer.

Preferably the solid insert is prepared from cellulose derivatives such as methyl cellulose, hydroxyethyl cellulose, hydroxypropyl cellulose or hydroxypropylmethyl cellulose or from other synthetic materials such as polyvinyl alcohol, polyvinyl pyrrollidone, polyethylene oxide or polyvinyl methylether. Hydroxypropyl cellulose, one of the preferred polymers for the preparation of the insert is available in several polymeric forms, all of which are suitable in the preparation of these inserts. Thus the product sold by Hercules, Inc. of Wilmington, Delaware under the name KLUCEL such as KLUCEL HF, HWF, MF, GF, JF, LF and EF which are intended for food or pharmaceutical use are particularly useful in preparing the inserts. The molecular weight of these polymers may be at least 30,000 to about 1,000,000 or more. Similarly, an ethylene oxide polymer having a molecular weight of up to 5,000,000 or greater, and preferably 100,000 to 5,000,000 can be employed. Further, for example, POLYOX a polymer supplied by Union Carbide Co. may be used having a molecular weight of about 50,000 to 5,000,000 or more and preferably 3,000,000 to 4,000,000. Other specific polymers which are useful in this invention are polyvinyl pyrrolidine having a molecular weight of from about 10,000 to about 1,000,000 or more, preferably up to about 350,000 and especially about 20,000 to 60,000; polyvinyl alcohol having a molecular weight of from about 30,000 to 1,000,000 or more, particularly about 400,000 and especially from about 100,000 to about 200,000; hydroxypropylmethyl cellulose having a molecular weight of from about 10,000 to 1,000,000 or more, particularly up to about 200,000 and especially about 80,000 to about 125,000; methyl cellulose having a molecular weight of from about 10,000 to about 1,000,000 or more, preferably up to about 200,000 and especially about 50 to 1,000,000; and CARBOPOL (carboxyvinyl polymer) of B. F. Goodrich and Co. designated as grades 934, 940 and 941. It is clear that for the purpose of this invention the molecular weight of the polymer is not critical. Water soluble polymers can be used having an average molecular weight which will afford dissolution of the polymer and medicament in any desired length of time. The inserts, therefore, can be prepared to allow for retention and accordingly effectiveness in the eye for any desired period.

The insert can be of any desired shape. Accordingly, the insert can be in the form of a square, rectangle, oval, circle, doughnut, semi-circle, ¼ moon shape, and the like. Preferably, the insert is in the form of a rod, doughnut, oval or ¼ moon. The insert can be readily prepared, for example, by dissolving the polymer and medicament in a suitable solvent and the solution evaporated to afford a thin film of the polymer which can then be subdivided to prepare inserts of appropriate size. Alternatively, the insert can be prepared by warming the polymer and medicament and then molded to form a thin film. Preferably, the inserts are prepared by molding or extrusion procedures well known in the art. The molded or extruded product can then be subdivided to afford inserts of suitable size for administration in the eye. For example, castings or compression molded films having a thickness of about 0.25 mm. to 15.0 mm. can be subdivided to obtain suitable inserts. Rectangular segments of the cast or compressed film having a thickness between about 0.5 and 1.5 mm. can be cut to afford shapes such as rectangular plates of 4 × 5–20 mm. or ovals of comparable sizes. Similarly, extruded rods having a diameter between about 0.5 and 1.5 mm. can be cut into suitable sections to provide the desired amount of polymer. For example, rods of 1.0 to 1.5 mm. in diameter and about 20 mm. long are found to be satisfactory. The inserts may also be directly formed by injection molding. It is preferred that the ophthalmic inserts of the present invention be formed so that they are smooth and do not have any sharp edges or corners which could cause damage to the eye. Since the term smooth and sharp edges or corners are subjective terms, in this application these terms are used to indicate that excessive irritation of the eye will not result from the use of the insert.

The ocular inserts containing the medicaments of this invention can also contain plasticizers, buffering agents and preservatives. The invention is therefore also directed to compositions containing these materials along with the water soluble polymer and medicament. Plasticizers suitable for this purpose must, of course, also be completely soluble in the lacrimal fluids of the eye. Examples of suitable plasticizers that might be mentioned are water, polyethylene glycol, propylene glycol, glycerine, trimethylol propane, di and tripropylene glycol, hydroxypropyl sucrose and the like. Typically, such plasticizers can be present in the ophthalmic insert in an amount ranging from up to 1 about 30% by weight. A particularly preferred plasticizer is water which is present in amounts of at least about 5% up to about 40%. In actual practice, a water content of from about 10% to about 20% is preferred since it may be easily accomplished and adds the desired softness and pliability to the insert.

When plasticizing the solid product with water, the product is contacted with air having a relative humidity of at least 40% until said product picks up at least about 5% water and becomes softer and more pliable. In a preferred embodiment, the relative humidity of the air is from about 60% to about 99% and the contacting is continued until the water is present in the product in amounts of from about 10% to about 20%.

Suitable water soluble preservatives which may be employed in the insert are sodium bisulfate, sodium thiosulfate, ascorbate, benzalkonium chloride, chlorobutanol, thimerosal, phenylmercuric acetate, phenylmercuric borate, parabens, benzyl alcohol and phenylethanol. These agents may be present in amounts of from 0.001 to 5% by weight of solid insert, and preferably 0.1 to 2%.

Suitable water soluble buffering agents are alkali, alkali earth carbonates, phosphates, bicarbonates, citrates, borates, and the like, such as sodium phosphate, citrate, borate, acetate, bicarbonate and carbonate. These agents may be present in amounts sufficient to obtain a pH of the system of between 5.5 to 8.0 especially 7–8; usually up to about 2% by weight of polymer. The insert may contain from about 1 mg. to 100 mg. and especially from 5 to 25 mg. The insert may contain from about 5 to 15% by weight of medicament. In the most preferred aspect, the insert contains about 5 to 15 mg. of water soluble polymer and 0.5 to 1.5 mg. of medicament.

A sustained miotic activity in rabbits associated with anti-glaucoma activity in man was observed for the compounds of this invention.

The novel compounds may be readily prepared by methods well known in the art for the preparation of acid addition salts. For example, pilocarpine free base may be added to an insert organic solvent such as ketones (acetone, methylethyl ketone), ethers (diethylether), alcohols (methanol, ethanol), nitriles (acetonitriles) and chloroform. This solution of pilocarpine may then be added to a soution of the acid required to form the apropriate acid addition salt. The solvent for the acid may be the same or different from that of the pilocarpine solution. All that is necessary is for the reactants to be in solution to obtain reaction. The reaction mixture is then stirred until reaction is complete. The reaction may take place at temperatures of from 0° C to the boiling point of the solvent, but preferably between 20° to 40° C. Reactants are suitably used in approximately equimolar amounts.

The following examples are given by way of illustration.

EXAMPLE 1

Pilocarpinium 2-naphtahalenesulfonate

A solution of 2.1 grams (10 millimole) of pilocarpine free base in 5 ml. of acetone is added to a solution of 2.26 g. (10 millimole) of 2-naphthalenesulfonic acid in acetone (40 ml.). The relsuting mixture is stirred at room temperature for 0.5 hour. The solvent is then removed by evaporation leaving a solid residue (3.9 g.) which is subsequently recrystallized from acetone to give 3.3 g. (79%) of pure pilocarpinium 2-naphthalenesulfonate, m.p. 129.5° to 130.5° C, $[\alpha]_D^{24} = + 49.0°$ (C=1.5, MeOH).

EXAMPLE 2

Pilocarpinium 3,5-di-tert-butylsalicylate

A solution of 2.1 grams (10 millimole) of pilocarpine free base in 5 ml. of acetone is added to a solution of 3,5-di-tert-butylsalicylic acid (2.50 g., 10 millimole) in acetone (30 ml.). The mixture is then diluted with 30 ml. of ether and 30 ml. of petroleum ether. The precipitated solid is collected by filtration. The filtrate is evaporated in vacuo leaving a white solid residue.

The two crops of crude solid salt are dissolved in 50 ml. of acetone and 30 ml. of ether is added. The reaction mixture is then cooled in a dry-ice bath and the flask vigorously scratched until solids begin to precipitate, then 20 ml. more of ether is added and the precipitated solid is quickly collected by filtration to give 4.3 g. (94%) of desired pilocarpinium 3,5-di-tert-butylsalicylate, m.p. 176° to 177° C, $[\alpha]_D^{24} = + 46.3°$ (C=1.4, MeOH).

EXAMPLE 3

Pilocarpinium 2-chloro-4,6-disulfamoylphenoxide

A solution of 0.73 gram (3.5 millimole) of pilocarpine free base in 5 ml. of acetone is added to a solution of 2-chloro-4,6-disulfamoylphenol (0.95 g., 3.31 millimole) in acetone (30 ml.). The resulting solution is stirred for 0.5 hour, the solvent is evaporated and the amorphous residue is redissolved in hot acetonitrile. The desired salt crystallizes after cooling and is collected by filtration to yield 1.5 g. (81%), m.p. 205° to 206° C, $[\alpha]_D^{24} = + 45.4°$ (C=0.5, $H_2O$).

EXAMPLE 4

Pilocarpinium 2,5-dihydroxybenzoate

A solution of 2.1 grams (10 millimole) of pilocarpine free base in 5 ml. of acetone is added to a solution of gentisic acid (1.54 g., 10 millimole) in acetone (30 ml.). The resulting mixture is stirred at room temperature for ½ hour. The solvent is evaporated giving a solid residue which is recrystallized from acetonitrile to give pure pilocarpinium 2,5-dihydroxybenzoate 3.3 g. (90%), m.p. 124° to 125° C, $[\alpha]_D^{24} = + 61.9°$ (C=0.6, $H_2O$).

EXAMPLE 5

Pilocarpinium dihydrogenphosphate

Pilocarpine free base (2.1 g., 10 millimole) is added to a stirred solution of phosphoric acid (0.98 g., 10 millimole) in methanol (8 ml.). The resulting turbid solution is stored at 10° C for 6 hours. The deposited white solid is collected and recrystallized from methanol (5 ml.) affording the title compound as colorless crystals, 1.4 g. (39%), m.p. 188°-189° C, $[\alpha]_D^{23} = + 73.91°$ (C=0.44, $H_2O$).

EXAMPLE 6

Pilocarpinium 2,5-dihydroxybenzoate equivalent to 2 mg. of pilocarpine base

Hydroxypropylcellulose (KLUCEL) q.s. and 12 mg.

Ophthalmic inserts are manufactured from compression molded films which are prepared on a Carver Press by subjecting the powder mixture of the above compounds to a compressional force of 12,000 lbs. (gauge) at 300° F for one to four minutes. The film is cooled under pressure by having cold water circulate in the platen. Ophthalmic inserts are then individually cut from the film with a rod shaped punch. Each insert is placed into a vial, which is then placed in a humidity cabinet (88% R.H. at 30° C) for two days. After removal from the humidity cabinet, the vials are stoppered and then capped. The vials containing the hydrated insert are then autoclaved at 250° C for 0.5 hour.

Similarly, when an equivalent amount of pilocarpinium 2-naphthalenesulfonate, pilocarpinium 2,5-dihydroxy-benzoate, pilocarpinium dihydrogenphosphate, pilocarpinium 2-chloro-4,6-disulfamoylphenoxide or pilocarpinium 3,5-di-tert-butylsalicylate is used in place of pilocarpinium 2,5-dihydroxybenzoate in the above example, similar inserts are obtained.

EXAMPLE 7

Pilocarpinium dihydrogenphosphate 0.02 grams as pilocarpine free base

Petrolatum q.a. ad 1 gram

The pilocarpinium dihydrogenphosphate is aseptically combined with sterile petrolatum.

EXAMPLE 8

Pilocarpinium 2-chloro-4,6-disulfamoylphenoxide: 1.0%
Sodium Citrate: 12 mg.
Citric Acid: 12 mg.
Disodium EDTA: 0.5 mg.
Tween 80: 2.0 mg.
Benzalkonium Chloride: 0.2 mg.
Sorbitol (70% solution): 10 mg.
Cellosize QP 100 ml.: 3 mg.
Water for injection q.s. ad: 1.0 ml.

Cellosize QP 100 ml. is dissolved in part of the water for injection. The solution is then passed through a coarse filter and autoclave to achieve sterility. To the other portion of water for injection there is added sodium citrate, citric acid, disodium EDTA, Tween 80, Sorbitol, Benzalkonium chloride and pilocarpine soluble salt. This solution is then passed through a sterilization pad (0.22 micron). The two sterile solutions are then aseptically combined.

What is claimed is:

1. Pilocarpinium 2,5-dihydroxybenzoate.

2. A topical ophthalmic composition comprising a topical ophthalmic vehicle and 1 to 15% of pilocarpinium 2,5-dihydroxybenzoate as medicament.

3. The ophthalmic composition of claim 2 wherein the vehicle is a water soluble solid polymer, said composition being in the form of a solid insert.

4. The composition of claim 5 wherein the water soluble solid polymer is hydroxypropyl cellulose.

5. The method of reducing intraocular pressure in the eye which comprises topically administering to an eye of a host having raised intraocular pressure an effective amount of pilocarpinium 2,5-dihydroxybenzoate.

* * * * *